US012661655B2

(12) United States Patent
Blain Christen

(10) Patent No.: US 12,661,655 B2
(45) Date of Patent: Jun. 23, 2026

(54) POINT OF NEED DIAGNOSTIC WITH THERMAL CONTROL

(71) Applicant: ARIZONA BOARD OF REGENTS ON BEHALF OF ARIZONA STATE UNIVERSITY, Scottsdale, AZ (US)

(72) Inventor: Jennifer Blain Christen, Chandler, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 642 days.

(21) Appl. No.: 18/009,475

(22) PCT Filed: Jun. 15, 2021

(86) PCT No.: PCT/US2021/037447
§ 371 (c)(1),
(2) Date: Dec. 9, 2022

(87) PCT Pub. No.: WO2021/257576
PCT Pub. Date: Dec. 23, 2021

(65) Prior Publication Data
US 2023/0143118 A1    May 11, 2023

Related U.S. Application Data

(60) Provisional application No. 63/039,208, filed on Jun. 15, 2020.

(51) Int. Cl.
*B01L 7/00* (2006.01)
*B01L 3/00* (2006.01)
*C12Q 1/6844* (2018.01)

(52) U.S. Cl.
CPC ............... *B01L 7/52* (2013.01); *B01L 3/5023* (2013.01); *C12Q 1/6844* (2013.01);
(Continued)

(58) Field of Classification Search
None
See application file for complete search history.

(56) References Cited

U.S. PATENT DOCUMENTS 9,805,165 B2    10/2017  Xiang et al.
10,519,492 B2 *  12/2019  DeJohn ............. B01L 3/502723
(Continued)

FOREIGN PATENT DOCUMENTS

WO      2013090394 A1      6/2013
WO      2014164933 A1      10/2014
WO      2016033646 A1      3/2016

OTHER PUBLICATIONS

Miralles et al., "A Review of Heating and Temperature Control in Microfluidic Systems: Techniques and Applications", Diangostics Jan. 15, 2013, 3, 33-67; doi:10.3390/diagnostics3010033.
(Continued)

*Primary Examiner* — Brian R Gordon
(74) *Attorney, Agent, or Firm* — Quarles & Brady LLP

(57) ABSTRACT
Provided herein are systems and methods for a point of need testing system. In some embodiments, the point of need testing system includes a first collector and a sample amplifier. The first collector is configured to collect a first biofluid sample. The sample amplifier includes an inlet dimensioned to receive the first biofluid sample. The sample amplifier further includes a filter, a heater, and a second collector. In some embodiments, a reader can be used with the sample amplifier to read a second biofluid produced by the sample amplifier.

11 Claims, 5 Drawing Sheets

(52) U.S. Cl.
CPC ..... *B01L 2200/026* (2013.01); *B01L 2200/10* (2013.01); *B01L 2200/16* (2013.01); *B01L 2300/0681* (2013.01); *B01L 2300/0825* (2013.01); *B01L 2300/1805* (2013.01); *B01L 2400/0457* (2013.01)

(56) References Cited

U.S. PATENT DOCUMENTS

| | | | |
|---|---|---|---|
| 10,591,474 B2 | 3/2020 | Katchman et al. | |
| 11,090,649 B2 * | 8/2021 | Linnes ................ | F16K 99/0032 |
| 11,162,130 B2 * | 11/2021 | Andreyev ............ | B01L 3/5027 |
| 12,023,672 B2 * | 7/2024 | Nowakowski .... | B01L 3/502761 |
| 12,128,414 B2 * | 10/2024 | Nowakowski ....... | C12Q 1/6816 |
| 2003/0225362 A1 * | 12/2003 | Currie ................. | A61B 5/6833 |
| | | | 604/20 |
| 2006/0257993 A1 | 11/2006 | McDevitt et al. | |
| 2014/0045191 A1 | 2/2014 | Dejohn et al. | |
| 2014/0112843 A1 * | 4/2014 | Thomas ................... | B01L 7/00 |
| | | | 422/549 |
| 2016/0216210 A1 * | 7/2016 | Jenkins ................. | C12Q 1/686 |
| 2016/0310948 A1 * | 10/2016 | Nowakowski ...... | B01L 3/50273 |
| 2018/0264464 A1 * | 9/2018 | Greef .................. | B01L 3/5023 |
| 2018/0304260 A1 * | 10/2018 | Thomas ............ | B01L 3/502761 |
| 2019/0032114 A1 * | 1/2019 | Trivedi ................ | B01L 3/5027 |
| 2019/0060895 A1 | 2/2019 | Myers, III et al. | |
| 2024/0033733 A1 * | 2/2024 | Thomas ............ | B01L 3/502761 |

OTHER PUBLICATIONS

International Search Report and Written Opinion issued in corresponding PCT Application No. PCT/US2021/037447, mailed Sep. 21, 2021.

* cited by examiner

104

108

POINT OF NEED DIAGNOSTIC WITH THERMAL CONTROL

CROSS-REFERENCE TO RELATED APPLICATIONS

This application is a national stage application filed under 35 U.S.C. § 371 of International Application No. PCT/US2021/037447, filed Jun. 15, 2021, which claims priority to U.S. provisional patent application No. 63/039,208, titled Point of Need Diagnostic with Thermal Control and filed Jun. 15, 2020, the entirety of which is incorporated herein by reference.

STATEMENT REGARDING FEDERALLY SPONSORED RESEARCH

Not applicable.

BACKGROUND

Centralized clinical testing of diagnostics is expensive and time consuming, causing delays in health care delivery. Often point of need testing and diagnostic assays lack the ability to provide quantitative and diagnostic information. In some cases, it may be useful in both clinical and non-clinical settings to provide a point of need testing system to address these and other issues.

BRIEF SUMMARY

The present disclosure provides, by way of various example embodiments, systems and methods for a point of need testing system. The point of need testing system includes a first collector and a sample amplifier. The first collector is configured to collect a first biofluid sample. The sample amplifier is configured for performing an amplification reaction to generate amplification products of a target nucleic acid to produce a second biofluid sample. The sample amplifier may comprise a reagent reservoir containing one or more reagents for performing the amplification reaction to generate amplification products of the target nucleic acid and, optionally, a control nucleic acid. The sample amplifier may further includes an inlet dimensioned to receive the first biofluid sample from the first collector, a filter, a heater, a second collector, or any combination thereof. In some embodiments, the sample amplifier further includes an indicator configured to produce an indication that the second biofluid sample has been produced from the first biofluid sample. In some embodiments, a reader can be used with the sample amplifier to read a second biofluid produced by the sample amplifier.

In some embodiments, a point of need testing system can include a reader. The ready may be configured to accept the second biofluid sample and produce an output. The reader can include a heater configured to heat the second biofluid sample, a lateral flow test strip, a detection site, an excitation array, a photodetector, or any combination thereof. In some embodiments, a photodetector can be configured to communicate a signal wirelessly.

In some embodiments, a point of need testing system includes a sample amplifier that is separate from the reader. The sample amplifier can be configured as a portable sample amplifier and the reader can be configured as a stationary reader so that the portable sample amplifier can be brought into contact with the stationary reader to accept the biofluid sample.

In some embodiments, a method of testing a biofluid sample is disclosed. The method includes collecting a first biofluid sample, filtering the first biofluid sample to remove particulate, heating the first biofluid sample in the presence of one or more reagents for performing an amplification reaction to generate amplification products of a target nucleic acid to produce a second biofluid sample; collecting the second biofluid sample, transporting the second biofluid sample to a detection site, irradiating the second biofluid sample at the detection site, and detecting emitted electromagnetic radiation indicative of the presence or absence of the target nucleic acid and, optionally, a control nucleic acid. The method may be performed with any of the point of need testing systems described herein.

In some embodiments, a method of testing a biofluid sample can include obtaining a first biofluid sample by inserting the biofluid into a biofluid collector. The method can include inserting the biofluid sample into a sample amplifier by rotating the biofluid collector and employing gravity to move the biofluid from the biofluid collector to the sample amplifier.

In some embodiments, a method of testing a biofluid sample can including transmitting a result to a processor. The method can also include decoding electromagnetic radiation intensity detected by a photodetector.

BRIEF DESCRIPTION OF THE DRAWINGS

The accompanying drawings, which are incorporated in and form a part of this specification, illustrate example embodiments of the invention and, together with the description, serve to explain the principles of certain embodiments.

DETAILED DESCRIPTION

Figure 1:
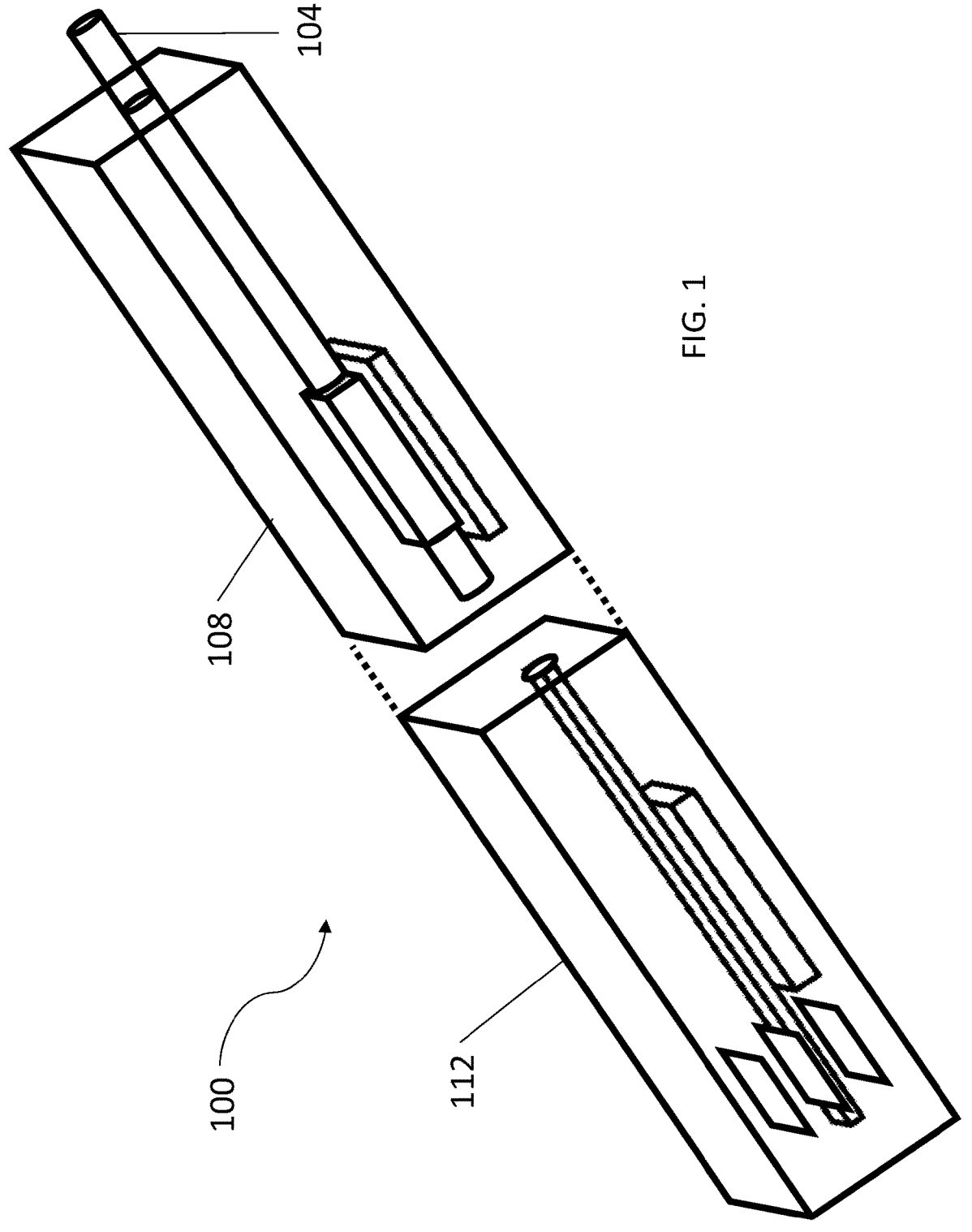
FIG. 1 is a schematic illustration of a point of need testing system including a biofluid collector, a sample amplifier, and a reader according to one embodiment of the invention.

The following discussion is presented to enable a person skilled in the art to make and use embodiments of the invention. Various modifications to the illustrated embodiments will be readily apparent to those skilled in the art after having studied the teachings in this disclosure, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans, after having studied the teachings in this disclosure, will recognize the examples provided herein have many useful alternatives and fall within the scope of embodiments of the invention.

A point of need (or point-of-care) testing system for use in clinical and non-clinical settings is described below. It can be generally useful to quantitatively test a biological fluid ("biofluid") sample. In some embodiments, the biofluid can include, without limitation, saliva, blood, serum, urine, cerebrospinal fluid, interstitial fluid, and other fluid samples. The point of need testing systems generally operate by detecting the presence or absence of a target nucleic acid. This may be accomplished by amplifying a target nucleic acid to prepare an amplification products that can be detected with a reader.

In particular embodiments, the testing system can be used to test a biofluid sample that has been allotted appropriate reaction time to amplify one or more target nucleic acids, including target nucleic acids indicative of potential pathogens, or control nucleic acids within the biofluid sample to generate amplification products. An "amplification product" or "amplicon" is a piece of nucleic acid that is the product of amplification or replication events. The amplification product may also be a source of further amplification or replication events. The "amplification" refers to production of one or more copies of nucleic acid sequence. Amplification of the nucleic acid sequence may be accomplished by various amplification methods known in the art including isothermal and non-isothermal amplification methods.

As used herein, "subject" or "patient" refers to mammals and non-mammals. A "mammal" may be any member of the class Mammalia including, but not limited to, humans, non-human primates (e.g., chimpanzees, other apes, and monkey species), farm animals (e.g., cattle, horses, sheep, goats, and swine), domestic animals (e.g., rabbits, dogs, and cats), or laboratory animals including rodents (e.g., rats, mice, and guinea pigs). Examples of non-mammals include, but are not limited to, birds, and the like. The term "subject" does not denote a particular age or sex. In one specific embodiment, a subject is a mammal, preferably a human. The subject may have or suffer from, or be suspected of having or suffering from, a disease, condition, or disorder.

In some embodiments, the subject may have or suffer from, or be suspected of having or suffering from, an infection by a pathogen. "Pathogen" means an organism that can produce disease in a subject. Examples of pathogens include, without limitation, viruses, bacteria, fungi, and parasites.

The target nucleic acid and the control nucleic acid can, but need not, originate from the same source. For example, the target nucleic acid may originate from a pathogen and the control nucleic acid may originate from the subject. In other embodiments, the both the target and control nucleic acids may originate from the subject. In yet other embodiments, the both the target and control nucleic acids may originate from a pathogen.

Some nucleic acid amplification processes can take close to an hour (e.g., approximately 45 minutes to 75 minutes) for target nucleic acids in a biofluid to be properly amplified into a detection sample. In some cases, it may be useful for a user to start the amplification process prior to arriving at a sample reader that reads the detection sample.

In some embodiments, the systems and devices of this disclosure are capable of analyzing samples at the point-of-need rather than in a laboratory. As used herein, the term "point of need" or "point of care" can be defined to mean a location on or near a site of patient care where medical or medically related services such as medical testing and/or treatment are provided, including but not limited to hospitals, emergency departments, intensive care units, primary care setting, medical centers, patient homes, physician offices, pharmacies, or sites of an emergency.

In some embodiments, the systems and devices of this disclosure are capable of analyzing samples to provide point-of-entry style testing. As used herein, the term "point of entry" can be defined as an entry point to a variety of workplaces or gathering locations, such as, for example, airports, train stations, nursing homes, schools, etc. Allowing for the testing of samples collected at or brought to the entry point aids in restricting access to the workplace or gathering location for those who test positive. Further, in some embodiments, the systems and devices of this disclosure are capable of analyzing samples at home to provide regular checks of individuals in a multi-family environment, such as assisted living facilities, dormitories, etc. In some embodiments, systems and devices of this disclosure include software that permits wirelessly transmitting test results to trusted parties including the individual being tested, the location allowing (or denying) entry, and healthcare entities.

The advantages of the systems and devices of this disclosure are multifold and include, for example, the benefit of shortening the time between sample collection and analysis, thereby identifying subjects having particular test results and, if appropriate, providing medical treatment sooner than traditionally possible with conventional diagnostic systems.

FIG. 1 illustrates a point of need testing system 100 according to one example embodiment of the invention. As illustrated in the example embodiment of FIG. 1, the point of need testing system 100 includes a biofluid collector 104, a sample amplifier 108, and a reader 112. In some embodiments, the sample amplifier 108 may be separate from the reader 112. In particular, the sample amplifier 108 may be portable, and can be transported to a final destination where the reader 112 resides. For example, a user may possess and travel with the sample amplifier 108 to a clinical or non-clinical destination, such as a hospital or an office, that has the reader 112. In other embodiments, the sample amplifier 108 can be fixed or removably coupled to the reader 112.

Figures 2, 3:
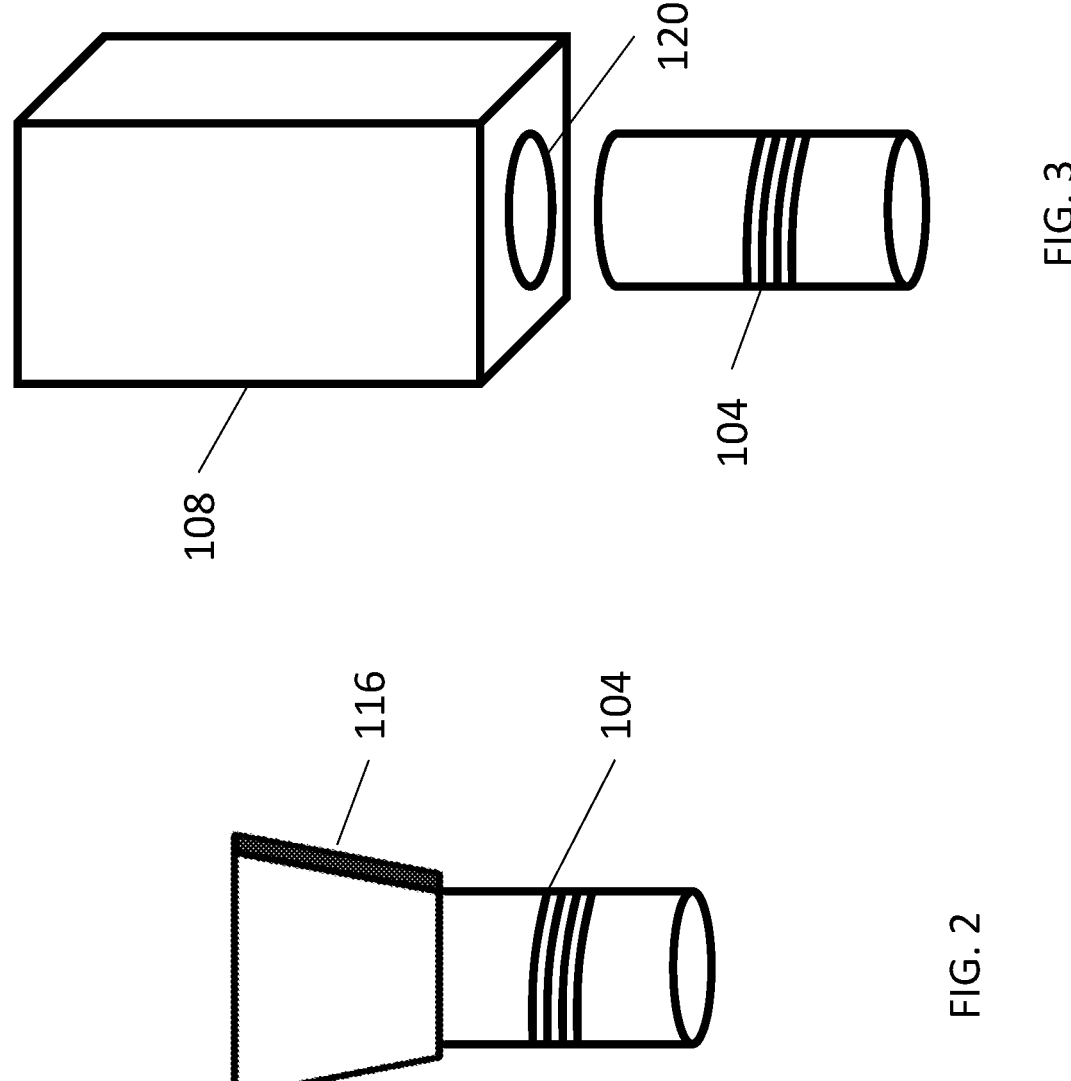
FIG. 2 is a schematic illustration of the biofluid collector of FIG. 1.
FIG. 3 is a schematic illustration of the biofluid collector and the sample amplifier of FIG. 1.

FIG. 2 illustrates the biofluid collector 104 of FIG. 1. The biofluid collector 104 can be fluidly coupled to a receiver 116 that provides a pathway between a user and the biofluid collector 104 for the biofluid to travel. In some embodiments, the receiver 116 may be dimensioned to facilitate the collection of particular biofluids, such as saliva. However, other configurations and biofluids are possible. For example, the receiver 116 may be configured as a cannulated needle configured to sample a biofluid from a user, including, without limitation, blood, serum, urine, cerebrospinal fluid, interstitial fluid, and other fluid samples, which may then be collected in the biofluid collector 104.

FIG. 3 illustrates the biofluid collector 104 and the sample amplifier 108 of FIG. 1. The sample amplifier includes a first 120 that is dimensioned to receive the biofluid collector 104, thereby fluidly coupling the biofluid collector 104 to the sample amplifier 108. In some embodiments, the biofluid collector 104 may include threads configured to engage threads of the sample amplifier 108 to secure the biofluid collector 104 to the sample amplifier 108. In other embodiments, the biofluid collector 104 may be secured to the sample amplifier 108 via additional (or alternative) coupling mechanisms such as press fit, snaps, and other latch and securement mechanisms. In some embodiments, the securement of the biofluid collector 104 to the sample amplifier 108 may permit and initiate the biofluid transfer from the biofluid collector 104 to the sample amplifier 108.

Figure 4:
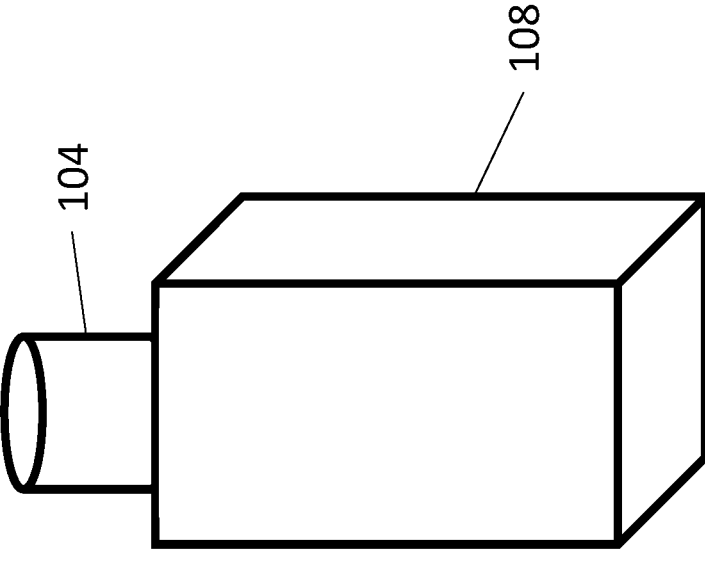
FIG. 4 is a schematic illustration of the biofluid collector coupled to the sample amplifier of FIG. 3.

Further illustrated in FIG. 3, in some embodiments the biofluid collector 104 is positioned, relatively speaking, below the sample amplifier 108 when in use by a user. As illustrated in FIG. 4, in use, once the biofluid collector 104 is secured to the sample amplifier 108, the sample amplifier 108 may be rotated 180 degrees relative to the orientation shown in FIG. 3. For example, as illustrated in FIG. 4, the biofluid collector 104 can be positioned above the sample amplifier 108 and gravity can be used to move biofluid from inside the biofluid collector 104 into the sample amplifier 108.

In other embodiments, sonication can be used to apply sound energy to agitate particles in the biofluid sample to move the biofluid sample from the biofluid collector 104 into the sample amplifier 108. In other embodiments, capillary flow may be used to induce a flow of the biofluid sample from the biofluid collector 104 to the sample amplifier 108. In other embodiments, a pressure difference created between the biofluid collector 104 and the sample amplifier 108 when the biofluid collector 104 is secured to the sample amplifier 108 can force the biofluid from the biofluid collector 104 to the sample amplifier 108.

Figures 5, 6:
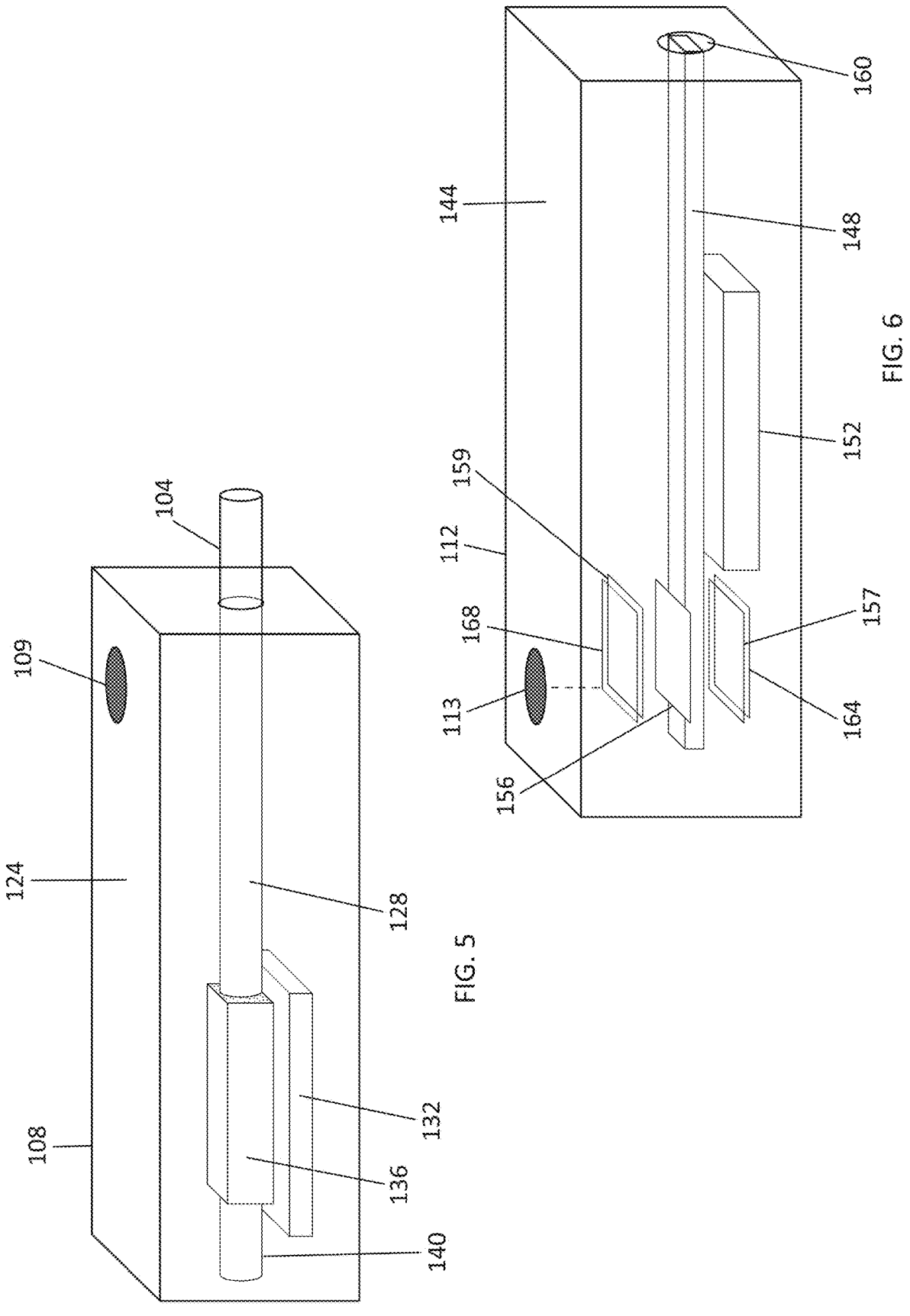
FIG. 5 is a detailed schematic illustration of the sample amplifier of FIG. 1.
FIG. 6 is a detailed schematic illustration of the reader of FIG. 1.

FIG. 5 illustrates the sample amplifier 108 with the biofluid collector 104 secured thereto. In general, the sample amplifier 108 can provide reagents for performing an amplification technique therein. Suitably, the amplification technique is an isothermal amplification technique. In some cases, the isothermal amplification technique is loop-mediated isothermal amplification (LAMP). Other isothermal amplification techniques may alternatively be used, and include, without limitation, strand displacement amplification (SDA), helicase-dependent amplification (HDA), nicking enzyme amplification reaction (NEAR), signal mediated amplification of RNA technology (SMART), rolling circle amplification (RCA), isothermal multiple displacement amplification (IMDA), single primer isothermal amplification (SPIA), recombinase polymerase amplification (RPA), polymerase spiral reaction (PSR), and reverse transcription polymerase chain reaction (RT-PCR). In some cases, reagents for isothermal amplification will vary based on the isothermal amplification technique employed and generally comprise primers and a strand-displacing DNA polymerase, a reverse transcriptase (for detection of RNA species), and/or a DNA helicase. In some cases, the reagents further comprise synthetic nucleic acids (e.g., riboregulators) configured to detect natural nucleic acids from one or more pathogens such as viruses, bacteria, fungi, and parasites.

In some embodiments, sample amplifier 108 may provide compounds or compositions suitable for use with point of need diagnostic devices or other biological assays. Suitably, the sample amplifier 108 may include, without limitation, buffers, surfactants, chaotropic salts, proteases such as poteninase K, chelating agents such as EDTA, co-factors, salts such as chaotropic salts, carrier RNA, or any combination thereof.

In the illustrated embodiment, the sample amplifier includes an amplifier housing 124 that houses a filter 128, an amplifier heater 132, a reagent reservoir 136, and a second biofluid collector 140. The amplifier housing 124 may selectively provide access to an interior of the amplifier housing 124 from an exterior of the amplifier housing 124. In some embodiments, access to the interior of the amplifier housing 124 can allow the user to remove, replace, dispose, and/or recharge certain components within the amplifier housing 124, as will be described in greater detail below.

The filter 128 in the illustrated embodiment is a filter configured to remove particulates from biofluid. In some embodiments, the filter is a mechanical, affinity, adsorption, or chemical bonding filter. As those of ordinary skill in the art will readily recognize and appreciate after having studied and benefited from the teachings in this disclosure, a variety of mechanical filters may be used, such as filter employing mesh membranes, beads, pores, or other filtering apparatuses. In some embodiments, particulates can include unwanted particles in the biofluid that are not useful to (or may hinder) amplifying nucleic acids in the biofluid. Such particles can include residual food particles from saliva, for example. The filter 128 may be disposable and replaceable within the sample amplifier 108 such that a user can remove the filter 128 after use and replace the filter 128 with an unused filter.

The amplifier heater 132 in the illustrated embodiment is configured to heat the biofluid sample within the sample amplifier 108. In some embodiments, the amplifier heater 132 may be reusable between biofluid samples within the amplifier housing 124. The heat provided by the amplifier heater 132 can accelerate the reaction kinetics of an amplification reaction of the target nucleic acid within the biofluid sample with reagents in the reagent reservoir 136.

The reagent reservoir 136 contains one or more reagents for performing an amplification technique therein to generate amplification products or amplicons of the target or control nucleic acid. Suitably, the reagent reservoir may contain a primer, a strand-displacing DNA polymerase, a reverse transcriptase, a DNA helicase, or any combination thereof. Like the filter 128, the reagent reservoir 136 may be disposable and replaceable within the sample amplifier 108 such that the user can remove the reagent reservoir 136 after use and replace the reagent reservoir 136 with an unused reservoir.

After a predetermined amount of time, the sample amplifier 108 can convert the biofluid sample into a second, processed biofluid sample which can be used as a detection sample as will be described below. The processed biofluid sample may contain amplification products or amplicons suitable for detection, thereby providing qualitative or quantitative information on the presence or absence of the target nucleic acid in the biofluid. The second biofluid collector 140 can collect (or receive) and retain the detection sample.

In some embodiments, the amplifier heater 132 may include a first heater and a second heater. The first heater may be placed proximate to a top of the biofluid sample and the second heater may be placed proximate to a bottom of the biofluid sample in the device. In an area that is proximate to the reagent reservoir 136, the biofluid sample may be surrounded by a thermally conductive material, such as copper, for example, to promote even heating provided by the amplifier heater 132 at the area proximate to the reagent reservoir 136.

In some embodiments, the sample amplifier 108 can further include a first indicator 109 as shown in FIG. 5. The indicator 109 can include one or more of an audio, visual, or tactile indication. For example, the indicator 109 may output a light (e.g., a green light) when a predetermined amount of time has passed from when the biofluid first entered the sample amplifier 108. In some embodiments, a user may initiate the sample amplifier via a start actuator, such as a button or a switch, for example, which begins the countdown from the predetermined amount of time. In other embodiments, a timer armed with the predetermined amount of time may be started once the biofluid collector 104 is secured to the sample amplifier 108. In some embodiments, the predetermined amount of time may be between approximately 15 minutes and 90 minutes. In other embodiments, the predetermined amount of time may be between approximately 30 minutes and 60 minutes. In general, the predetermined amount of time is the time required for the biofluid to be reacted and amplified such that the detection sample can be read by the reader 112.

FIG. 6 illustrates the reader 112 of FIG. 1. In general, the reader is configured to accept (or receive) the detection sample and produce a qualitative or quantitative output. In the embodiment shown, the reader 112 includes a reader housing 144 that houses a lateral flow strip 148, a reader heater 152, and a detection site 156. The reader housing 144 may selectively provide access to an interior of the reader housing 144 from an exterior of the reader housing 144. In some embodiments, access to the interior of the reader housing 144 can allow the user to remove, replace, dispose, and/or recharge certain components within the reader housing 144, as will be described in greater detail below. The reader 112 further includes a second inlet 160 that is dimensioned to receive the detection sample from the second biofluid collector 140.

The lateral flow strip 148 is proximate to the second inlet 160 and can transport the detection sample from the second biofluid collector 140 to the detection site 156. The lateral flow strip 148 enables flow through capillary forces. In alternative embodiments, a channel that allows for flow driven by pressure may substitute for the lateral flow strop. Suitably, the lateral flow strip 148 or channel may include reagents, such as reagents for performing an amplification technique or compounds or compositions suitable for use with point of need diagnostic devices or other biological assays. The second biofluid collector 140 may include a paper-based membrane or microfluidic channel that is configured to induce capillary flow from the second biofluid collector 140 to the lateral flow strip 148. In some embodiments, the reader heater 152 may heat the detection sample as the detection sample is transported along the lateral flow strip 148 and is received at the detection site 156. Heating the lateral flow strip 148 or detection site 156 allows for the amplification reaction to be accomplished in whole or in part within the lateral flow strip 148 or detection site 156.

The detection site 156 can be positioned between an excitation array 164 and a photodetector 168. Optionally, a first optical filter 157 may be positioned between the excitation array 164 and the detection site 156 or a second optical filter 159 may be positioned between the detection site 156 and the photodetector 168 as shown in FIG. 6. In some embodiments, the first and second optical filters 157, 159 are positioned between excitation array 164 and the detection site 156 and the detection site 156 and the photodetector 168.

The excitation array 164 provides electromagnetic radiation that may be absorbed by the detection sample. The electromagnetic radiation may be of any suitable wavelength that can provide a detectable signal indicating the presence or absence of an amplification product of a target nucleic acid. In some embodiments, the electromagnetic radiation may be of any suitable wavelength that can provide a detectable signal indicating the presence or absence of an amplification product of a control nucleic acid. In some embodiments, the excitation array 164 provides electromagnetic radiation in the infrared, visible, or ultraviolet spectrums. The excitation array 164 may emit broadband or narrowband electromagnetic spectrums. A first optical filter 157 provided between the excitation array 164 and the detection site 156 may be used to selectively provide the wavelengths within a desired spectral window to the detection site 156.

The photodetector 168 may detect any suitable wavelength or electromagnetic radiation. In some embodiments, the photodetector 168 detects electromagnetic radiation in the infrared, visible, or ultraviolet spectrums. The photodetector 168 may include an array connected to a readout circuit, which can include a microchip. The photodetector 168 can wirelessly or wiredly communicate to a processor (not shown) that can decode and translate intensities sent via a digital signal that originate from a current signal. The detection sample may include biomarkers, chromophores, fluorophores, dyes, and other compounds or substances capable of emit light of a second wavelength or color when stimulated by a first light of a first wavelength or color. The presence of amplification products of the target and/or control nucleic acid sequence in the second biofluid sample may alter electromagnetic radiation intensity emitted at the second wavelength relative to an amplification product free second biofluid sample. The photodetector 168 can detect the light of the second color and output the current which is then transmitted to the processor. The intensity of the detected light allows for determination of the presence or absence of the target nucleic acid and/or control nucleic acid target. The processor can output qualitative or quantitative results that can be used for epidemiological data collection and studies.

A second optical filter 159 provided between the detection site 156 and the photodetector 168 may be used to select selectively provide wavelengths within a desired spectral window to the photodetector 168. When the first and second optical filters 157, 159 are positioned between excitation array 164 and the detection site 156 and the detection site 156 and the photodetector 168, the first optical filter 157 positioned between excitation array 164 and the detection site 156 may selectively provide the wavelength of the first color and the second optical filter 159 positioned between the detection site 156 and the photodetector 168 may selectively provide the wavelength of the second color. Such an embodiment may minimize the electromagnetic radiation provided by the excitation array 164 being provided directly to the photodetector 168.

In some embodiments, the reader 112 can further include an second indicator 113 as shown in FIG. 6. The second indicator 113 can include one or more of an audio, visual, or tactile indication. For example, second indicator 113 may output a light (e.g., a green light or a red light) if a specific pathogen at a predetermined level is found (or not found) in the detection sample. Similar to the sample amplifier 108, elements of the reader 112 may be reusable. For example, the heater and components of the detection site 156 such as the photodetector, excitation array, and the microchip. Correspondingly, the lateral flow strip 148 may be replaceable within the reader housing 144 which can be selectively accessible from the outside.

Figure 7:
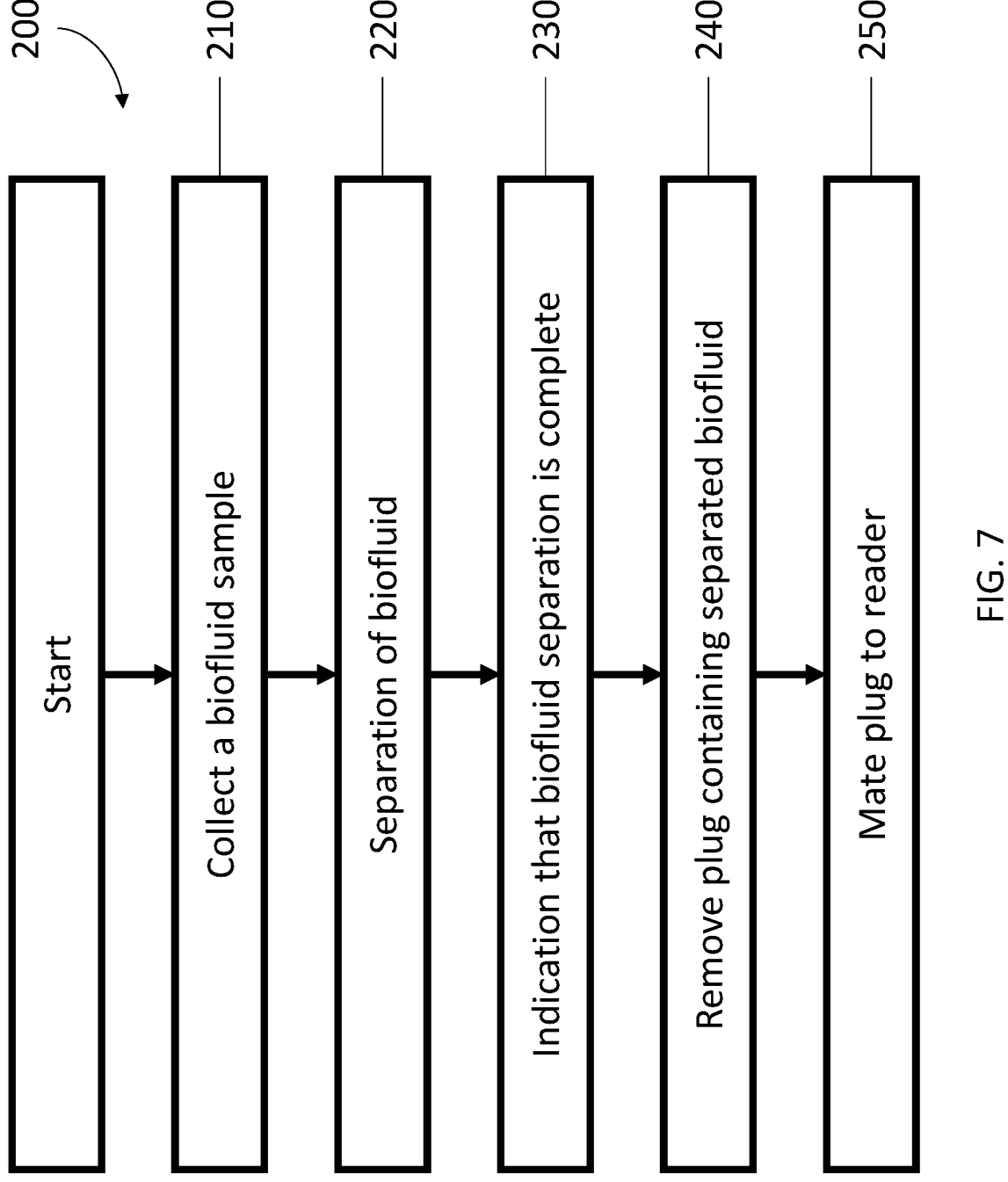
FIG. 7 is a flowchart illustrating an example of a method of a point of need testing system according to some embodiments.

FIG. 7 illustrates a flowchart 200 of an example method of use of a point of need testing system, similar to the point of need testing system 100 described above. In use, a user may collect a biofluid sample in a sample collector, as indicated in 210. The biofluid may then be separated via a first device to form a second biofluid, as indicated in step 220. The second biofluid may be an amplified version of the first biofluid that has undergone a reaction with heat and/or reagents. After a predetermined amount of time has passed, an indicator may indicate that the biofluid sample is successfully separated into the second biofluid, as indicated in step 230. A plug or second sample collector that contains the second biofluid may be removed from the first device as indicated in step 240. In some embodiments, the plug or second sample collector may be removed from the first device via a Leur or compression-style system. The plug or second sample collector may then be mated to a second device as indicated in step 250. The second device may be a reader with a photodetector configured to detect pathogens in the biofluid sample and provide an output to an indicator on the reader and/or send the output wirelessly to a processor that includes quantitative data.

In some embodiments, the first device of the method 200 may be separate from the second device. However, in other embodiments, the first device may be fluidly coupled to the second device such that steps 240 and 250 of the method 200 are unnecessary.

The previous description of the disclosed embodiments is provided to enable any person skilled in the art to make or use the invention. Various modifications to these embodiments will be readily apparent to those skilled in the art, and the generic principles defined herein may be applied to other embodiments without departing from the spirit or scope of the invention. Thus, the invention is not intended to be limited to the embodiments shown herein but is to be accorded the widest scope consistent with the principles and novel features disclosed herein.

I claim:

1. A point of need testing system comprising:
a first collector configured to collect a first biofluid sample;
a sample amplifier configured for performing an amplification reaction to generate amplification products of a target nucleic acid to produce a second biofluid sample, the sample amplifier comprising:
a first inlet;
wherein the sample amplifier is fluidly coupled to the first collector by the first inlet,
wherein the first inlet is dimensioned to receive the first biofluid sample from the first collector;
a reagent reservoir containing one or more reagents for performing the amplification reaction to generate amplification products of the target nucleic acid;
a filter fluidly coupled to the first collector and to the reagent reservoir, and configured to remove particulates from the first biofluid sample;
an amplifier heater positioned adjacent to the reagent reservoir and configured to accelerate reaction kinetics of the amplification reaction of the target nucleic acid within the first biofluid sample to produce the second biofluid sample;
a sample amplifier housing,
wherein the filter, the reagent reservoir, and the amplifier heater are disposed within the sample amplifier housing,
a second collector removably coupled to the reagent reservoir and configured to collect the second biofluid sample;
an excitation array;
a photodetector; and
a reader configured to accept the second biofluid sample and produce an output, the reader comprising:
a second inlet dimensioned to receive the second biofluid sample from the second biofluid collector;
a lateral flow test strip coupled to the second inlet and configured to transport the second biofluid sample from the second inlet to a detection site positioned between the excitation array and the photodetector;

wherein the excitation array is arranged to irradiate the detection site and the photodetector is arranged to detect electromagnetic radiation emitted from the detection site and configured to produce the output;
a reader heater positioned adjacent to the lateral flow test strip configured to heat the second biofluid sample transporting along the lateral flow test strip; and
a reader housing, wherein the lateral flow test strip, the detection site, and the reader heater are disposed within the reader housing.

2. The point of need testing system of claim 1, wherein the photodetector is configured to detect a signal from the second biofluid sample at the detection site, wherein the second biofluid sample comprises amplification products of the target nucleic acid, wherein the target nucleic acid originates from a pathogen.

3. The point of need testing system of claim 1, wherein the reagent reservoir contains one or more reagents for performing an amplification reaction to generate amplification products of a control nucleic acid and the amplifier heater is configured to accelerate reaction kinetics of the amplification reaction of the control nucleic acid within the first biofluid sample to produce the second biofluid sample.

4. The point of need testing system of claim 3, wherein the photodetector is configured to detect a signal from a detection sample at the detection site, wherein the detection sample comprises amplification products of the control nucleic acid originating from a subject and the target nucleic acid originating from a pathogen.

5. The point of need testing system of claim 1, wherein the sample amplifier is removably coupled to the reader.

6. The point of need testing system of claim 5, wherein the sample amplifier is configured as a portable sample amplifier and the reader is configured as a stationary reader so that the portable sample amplifier can be brought into contact with the stationary reader such that the stationary reader accepts the second biofluid sample from the portable sample amplifier.

7. The point of need testing system of claim 1, wherein the sample amplifier includes an indicator configured to produce an indication that the second biofluid sample has been produced from the first biofluid sample.

8. The point of need testing system of claim 1, wherein the photodetector is configured to communicate a signal wirelessly.

9. The point of need testing system of claim 1, wherein the reader further comprises:
a first optical filter positioned between the excitation array and the detection site; the first optical filter is arranged to selectively provide the detection site with a first wavelength of electromagnetic radiation from the excitation array; and
a second optical filter positioned between the detection site and the photodetector; the second optical filter is arranged to selectively provide a second wavelength of electromagnetic radiation emitted from the detection site to the photodetector.

10. The point of need testing system of claim 9, wherein the photodetector is configured to detect the presence of amplification products of the target nucleic acid in the second biofluid sample as altered electromagnetic radiation intensity emitted at the second wavelength relative to an amplification product free second biofluid sample.

11. The point of need testing system of claim 1, wherein the amplifier heater is configured to provide heat for an isothermal application reaction.

* * * * *